(12) United States Patent
Sogard (10) Patent No.: US 8,940,012 B2
(45) Date of Patent: Jan. 27, 2015

(54) INTRAVASCULAR FILTER WITH BIODEGRADABLE FORCE-REDUCING ELEMENT

(75) Inventor: David J. Sogard, Edina, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 557 days.

(21) Appl. No.: 13/274,498

(22) Filed: Oct. 17, 2011

(65) Prior Publication Data

US 2012/0143238 A1 Jun. 7, 2012

Related U.S. Application Data

(60) Provisional application No. 61/420,579, filed on Dec. 7, 2010.

(51) Int. Cl.
*A61F 2/01* (2006.01)

(52) U.S. Cl.
CPC ............. *A61F 2/01* (2013.01); *A61F 2002/016* (2013.01); *A61F 2250/0031* (2013.01); *A61F 2230/005* (2013.01); *A61F 2230/0067* (2013.01)
USPC ............................ 606/200; 606/191; 606/198

(58) Field of Classification Search
None
See application file for complete search history.

(56) References Cited

U.S. PATENT DOCUMENTS

| 5,776,162 | A | 7/1998 | Kleshinski | |
|---|---|---|---|---|
| 6,342,063 | B1 | 1/2002 | DeVries et al. | |
| 6,416,530 | B2 | 7/2002 | DeVries et al. | |
| 6,468,226 | B1 | 10/2002 | McIntyre, IV | |
| 6,663,664 | B1* | 12/2003 | Pacetti | 623/1.2 |
| 6,805,705 | B2 | 10/2004 | Hong et al. | |
| 6,972,025 | B2 | 12/2005 | WasDyke | |
| 7,141,063 | B2* | 11/2006 | White et al. | 623/1.15 |
| 7,534,251 | B2 | 5/2009 | WasDyke | |
| 8,092,484 | B2* | 1/2012 | Kashkarov et al. | 606/200 |
| 2003/0212449 | A1 | 11/2003 | Cox | |
| 2005/0277977 | A1 | 12/2005 | Thornton | |
| 2006/0015137 | A1 | 1/2006 | WasDyke et al. | |
| 2007/0141106 | A1* | 6/2007 | Bonutti et al. | 424/423 |
| 2008/0027481 | A1 | 1/2008 | Gilson et al. | |

(Continued)

FOREIGN PATENT DOCUMENTS

| EP | 0350043 B1 | 1/1990 |
|---|---|---|
| EP | 1258228 A1 | 11/2002 |

(Continued)

*Primary Examiner* — Melanie Tyson
*Assistant Examiner* — Todd J Scherbel
(74) *Attorney, Agent, or Firm* — Seager, Tufte & Wickhem LLC (57) ABSTRACT

An intravascular filter for a vessel includes a non-biodegradable apical hub and non-biodegradable struts extending generally distally from the hub. The struts extend radially outward from a longitudinal axis of the hub. The distal ends of the struts exert an expansile force against an interior of the vessel. One or more struts includes one or more time-degrading connectors along its length, which can be formed from a biodegradable element made from a fixation material. Prior to degradation, the fixation material rigidly connects a proximal section to a distal section of the respective strut. After degradation, the fixation material is dissolved or softened, and reveals a link that has a strong resistance to longitudinal movement of the distal section with respect to the proximal section and may have a weak resistance to rotational movement of the distal section with respect to the proximal section, such as a pair of interlocked loops.

18 Claims, 8 Drawing Sheets

(56) References Cited

U.S. PATENT DOCUMENTS

| | | |
|---|---|---|
| 2009/0270901 A1 | 10/2009 | Kelleher et al. |
| 2009/0275971 A1 | 11/2009 | Kelleher et al. |
| 2010/0063572 A1 | 3/2010 | Teoh et al. |
| 2010/0234935 A1 | 9/2010 | Bashiri et al. |
| 2010/0241215 A1 | 9/2010 | Hansen et al. |

FOREIGN PATENT DOCUMENTS

| | | | |
|---|---|---|---|
| WO | WO2007/079407 | * | 7/2007 |
| WO | 2008015257 A2 | | 2/2008 |

* cited by examiner

INTRAVASCULAR FILTER WITH BIODEGRADABLE FORCE-REDUCING ELEMENT

RELATED APPLICATIONS

This application claims priority to U.S. Provisional Application Ser. No. 61/420,579 filed Dec. 7, 2010.

TECHNICAL FIELD

The present invention relates generally to the field of medical devices. More specifically, the present invention pertains to intravascular filters implantable within a body vessel.

BACKGROUND

Blood clot filters are typically used in conjunction with thrombolytic agents and anti-coagulants to treat pulmonary embolism occurring within a patient. These devices are generally implanted within a vessel such as the inferior vena cava, and function by capturing blood clots (emboli) contained in the blood stream before they can reach the lungs and cause permanent damage to the body. To filter emboli, many conventional blood clot filters utilize a number of independent filter legs coupled to an apical head that can be expanded within the body to form a conical-shaped surface that collects the emboli without disturbing the flow of blood. Once collected, a natural clot lysing process occurs within the body to dissolve the emboli collected by the filter.

Delivery of the blood clot filter within the body is generally accomplished via an introducer sheath percutaneously inserted through the femoral (groin) or jugular (neck) veins. Such introducer sheaths are generally tubular in shape, and include an inner lumen configured to transport the filter in a collapsed position through the body. Once transported to a desired location within the body, the filter can then be removed from within the introducer sheath, allowing the filter legs to spring open and engage the vessel wall. A needle, hook, barb, prong, wedge or other attachment means disposed on the base of each filter leg can be used to secure the filter within the vessel.

The filter legs exert an expansile force, directed radially outward against the vessel wall. Particularly in thinner walled vessels, prolonged application of such expansile forces on a relative small surface area on the vessel wall can lead to undesirable tissue movements, such as the hooks migrating through the vessel wall. When a particular filter, such as a vena cava filter, is to be removed, the radial expansion forces and resulting tissue changes may make the filter removal difficult.

Accordingly, there exists a need for improved filter anchoring that can avoid complications, trauma and removal difficulties related to continued strong expansion forces.

SUMMARY

The present invention pertains to a bioabsorbable or biodegradable element that reduces over time the expansile forces exerted by an intravascular filter within a vessel.

An embodiment of an intravascular filter for a vessel includes a non-biodegradable apical hub; a plurality of non-biodegradable struts, each strut having a proximal section secured to the apical hub, each strut having a distal section extending generally distally away from the apical hub and extending radially outward from a longitudinal axis of the apical hub, the respective distal sections of the struts exerting an expansile force against an interior of the vessel; and at least one biodegradable element disposed along at least one strut, the biodegradable element maintaining the expansile force prior to degradation and reducing the expansile force after degradation.

Another embodiment of an intravascular filter for a vessel includes a non-biodegradable proximal apical hub; a non-biodegradable distal apical hub; a plurality of non-biodegradable struts, each strut having a proximal section secured to the proximal apical hub, each strut having a distal section secured to the distal apical hub, each strut having a central section between the proximal section and the distal section, a central portion of the central section extending generally parallel to a longitudinal axis connecting the proximal and distal apical hubs, the central portions of the struts being arranged circumferentially within an interior of the vessel, the central portions exerting an expansile force against the interior of the vessel; and at least one biodegradable element disposed along at least one strut, the biodegradable element maintaining the expansile force prior to degradation and reducing the expansile force after degradation.

Another embodiment of an intravascular filter for a vessel includes a non-biodegradable apical hub; a plurality of non-biodegradable struts, each strut having a proximal section secured to the apical hub, each strut having a distal section extending generally distally away from the apical hub and extending radially outward from a longitudinal axis of the apical hub, the respective distal sections of the struts exerting an expansile force against an interior of the vessel; and a plurality of biodegradable elements, each biodegradable element in the plurality disposed along a respective strut between the respective proximal section and the respective distal section, the biodegradable elements comprising a fixation material that, prior to degradation, fixes in place a link between the proximal section and the distal section, the link having strong resistance to longitudinal movement of the distal section with respect to the proximal section, the link having weak resistance to rotational movement of the distal section with respect to the proximal section.

BRIEF DESCRIPTION OF THE FIGURES

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

In at least some embodiments, an intravascular filter for a vessel includes a non-biodegradable apical hub and non-biodegradable struts extending generally distally from the hub. The struts extend radially outward from a longitudinal axis of the hub. The distal ends of the struts exert an expansile force against an interior of the vessel. One or more struts includes one or more time-degrading connectors along its length, which can be formed from a biodegradable element made from a fixation material. Prior to degradation, the fixation material rigidly connects a proximal section to a distal section of the respective strut. After degradation, the fixation material is dissolved or softened, and reveals a link that may have a strong resistance to longitudinal movement of the distal section with respect to the proximal section and may have a weak resistance to rotational movement of the distal section with respect to the proximal section. One suitable link includes a pair of interlocked loops, with one loop in the pair on the proximal section and the other loop in the pair on the distal section. Another suitable link includes a narrowed portion between the proximal and distal sections of the strut.

A typical vena cava filter uses an expansion force of anchor barbs or hooks, pads or stent struts to secure the filter in place in the vena cava. After a period of tissue healing occurs, less outward force is required to maintain the filter securely in place. While typical known vena cava filter anchors continue to exert outward force on the vein wall, the filter described herein uses one or more biodegradable elements to reduce over time the outward force on the vein wall. Over time, the filter decreases the outward force exerted on vena cava filter anchors to prevent migration of the wires through the vein wall. By reducing over time the outward force applied onto a vein wall, stents, filters and other thin structures can be prevented from migrating though a vein wall over time and ending up partly or completely on the outside of the vein.

The biodegradable elements described herein may be used with any suitable intravascular filter that uses a series of struts to exert a force radially outward against an interior of a vessel. For instance, one suitable filter is disclosed in U.S. Pat. No. 6,972,025, issued on Dec. 6, 2005 to Joel M. WasDyke, titled "Intravascular filter with bioabsorbable centering element" and assigned to SciMed Life System, Inc. in Maple Grove, Minn. In patent '025, the filter legs denoted by element number 16 are suitable to receive such a biodegradable element, as described herein. It will be appreciated that the filter legs, wires or struts may have any suitable configuration, extending distally or proximally from the hub, optionally including any number of bends, twists, turns or branches, extending through a vessel wall, terminating proximate the vessel wall or continuing past the vessel wall to loop back on themselves, reattach to a hub or attach to a second hub.

Figure 1:
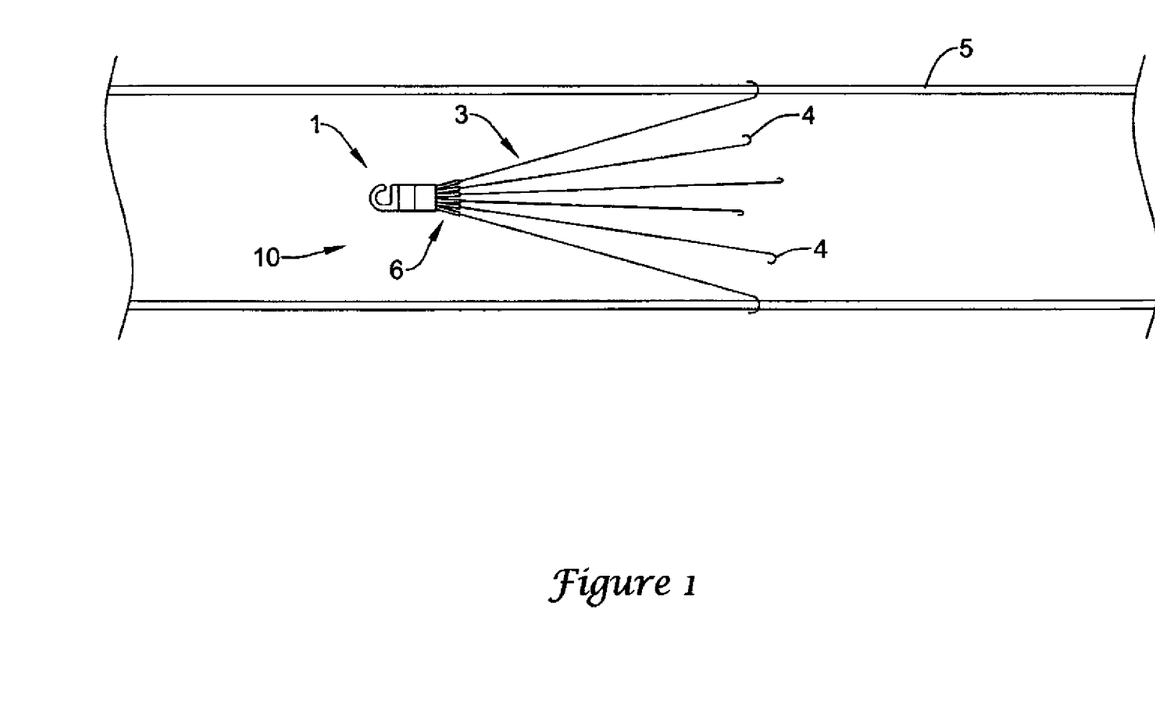
FIG. 1 is a side-view schematic drawing of an intravascular filter inside a vessel, with struts exerting a radially expanding force against the inside of the vessel wall.

FIG. 1 is a side-view schematic drawing of an intravascular filter 10 inside a vessel, with struts or wires 3 exerting a radially expanding force against the inside of the vessel wall 5. The struts 3 are generally non-biodegradable, and extend generally distally from an apical hub 1, which is also generally non-biodegradable. At the distal ends of the struts 3 are anchors or hooks 4 that extend through the wall 5 of the vessel.

As used herein, the term "generally distally" is defined as follows. Note that if the struts were to extend "strictly distally", the struts would all emerge from the hub 1 parallel to each other and to the longitudinal axis of the hub, would extend distally all parallel to each other without bending, and would remain generally in a bundle sized to match the footprint of the hub 1 along their entire lengths. The term "generally distally" is intended herein to mean "not strictly distally", in that each struts may bend sharply and/or bend with a gradual curvature at one or more points along its length, and/or may emerge from the hub with a divergent angle with respect to the longitudinal axis of the hub 1. In general, for the struts extending "generally distally" from the hub 1, the distal ends of the struts are located distal to the proximal ends of the struts, are located distal to the hub 1, and also subtend a larger footprint than that of the hub 1.

In the configuration of FIG. 1, the filter includes flexing or pivoting links between each anchor 4 and the hub 1 or main body of the filter 10. The links structurally communicate expansile anchoring force to the anchors 4. For initial deployment and anchoring, the links are held fixed by a fixation material, which reduces the flexing or pivoting of the links to exert a higher expansile force on the anchors for robust initial anchoring. Note that in FIG. 1, the links and fixation material, taken together, are represented by element number 6, and are referred to herein as a time-degrading connector 6.

The fixation material dissolves or softens over time by standard degradation mechanisms, such as with degradable polymers like PGA, LFGA, and so forth. After the fixation dissolves or softens, the links are free to flex or pivot, thereby decreasing the expansile force on the anchors. FIG. 1 has the struts 3 arranged in a configuration commonly referred to as "wire cone", although other suitable configurations may be used.

In the design if FIG. 1, the links and fixation material are located near the apical hub 1. It is understood that the links and fixation material may be located at any suitable location along the strut, including at the hub 1, directly adjacent to the hub 1, adjacent to the hub 1, away from the hub 1, between the hub and anchor 4, adjacent to the anchor 4, directly adjacent to the anchor 4, and at the anchor 4. In each case, the link is said to be disposed between proximal and distal sections of the strut 3. The proximal and distal sections of the strut 3 may be the same lengths, or may be different lengths. In some cases, when the links and fixation material are at the hub 1 or the anchor 4, the proximal or distal sections of the strut 3 may be relatively short or even non-existent if a portion of the link attaches directly to the hub 1 or the anchor 4.

In some cases, the link and fixation material are located at the same longitudinal location on each strut, for all the struts in the filter 10. In other cases, at least some of the link and fixation material have their locations vary from strut-to-strut in the filter 10. In all cases, the link and fixation material are located together on the respective strut, as shown and described in the following figures.

The fixation material is a suitable biocompatible material configured to degrade within the body within a predetermined period of time. While a variety of materials are capable of degrading within the body, a biodegradable material in accordance as used herein is understood to be one that is capable of degradation in vivo within a few days up to a number of years. Examples of suitable biodegradable materials may include, but are not limited to, polylactic acid (PLA), polyglycolic acid (PGA), copolymer poly(lactide-co-glycolide) (PLGA), polydioxanone, polyanhydrides, trimethylene carbondate, poly(hydroxybutyrate), poly(g-ethyl glutamate), poly(ortho esters), polycyanoacrylate, polyphosphazenes, poly(a-hydroxy acids), poly(e-caprolactone), polysaccharides (e.g. cellulose, chitin, dextran), modified proteins (e.g. fibrin, casein), albumin, collagen, gelatin, alginate, starch, and/or copolymers, mixtures or combinations thereof.

The degradation time of the material varies depending in part on the type of material employed. To permit the fixation material to function during the initial period of implantation, and for the days shortly thereafter when migration of the filter within the vessel is most likely, a degradation time lasting approximately 20-30 days is generally sufficient. In certain cases, however, quicker degradation times of about three to five days may be desirable.

The period of time that the fixation material remains functional within the vessel is dependent in part upon a number of intrinsic and extrinsic design factors. Intrinsic factors such as the absorption rate of the material(s) employed and the specific geometry of the fixation material may affect the period of time necessary for the fixation material to degrade in the body. Factors unique to the fixation material such as the level of crystallinity, orientation, substituents and molecular weight, for example, may have an impact on the period of time required for the material to degrade in vivo. Extrinsic factors such as the pH of the biological medium, electrolytes, external stress, temperature, radiation, free radicals, and enzymes may also affect the degradation time of the fixation material in vivo. Other environmental factors such as material processing, sterilization, and storage may affect the degradation time of the fixation material.

Based on a given set of extrinsic and intrinsic conditions, a specific absorption rate may be designed by utilizing materials with either a fast degradation rate or a slow degradation rate. For example, biodegradable materials having a relatively low molecular weight can be employed to increase the rate at which the fixation material degrades within the body. Mechanical properties such as tensile strength and bendability may also be altered by selecting materials having a particular level of crystallinity or other intrinsic characteristic.

The degradation of absorbable polymers is due primarily to hydrolysis. A hydrolytic reaction causes the molecular chains of the polymer to break down and the chain length to decrease. This process results in a reduction in the physical and mechanical properties of the material over time. A loss of mass occurs when a significant number of chains are broken to allow diffusion of small molecular chains out of the polymer and into the environment. Disintegration of the polymer finally occurs when there has been a loss in strength and mass, and portions of the polymer become detached. With certain materials, this hydrolytic reaction forms by-products that can be easily metabolized and/or excreted within the body. With bioabsorbable PGA or PLLA, for example, a hydrolytic chain scission occurs within the body to produce lactic and glycolic acid. These acids are then metabolized by the surrounding tissue and fluids and converted (via a citrate cycle) into carbon dioxide that can be easily eliminated from the body via respiration.

Degradation of absorbable polymers tends to be non-homogeneous since such materials are generally semi-crystalline in structure, and thus exhibit both amorphous and crystalline regions. Since degradation occurs more rapidly at the amorphous regions rather than at the crystalline regions, a decrease in tensile strength in the fixation material generally occurs prior to a decrease in mass. This loss in tensile strength occurs prior to the loss of mass since the fixation material degrades through its bulk (i.e. in an inside-out manner) rather than from surface erosion.

Figure 2:
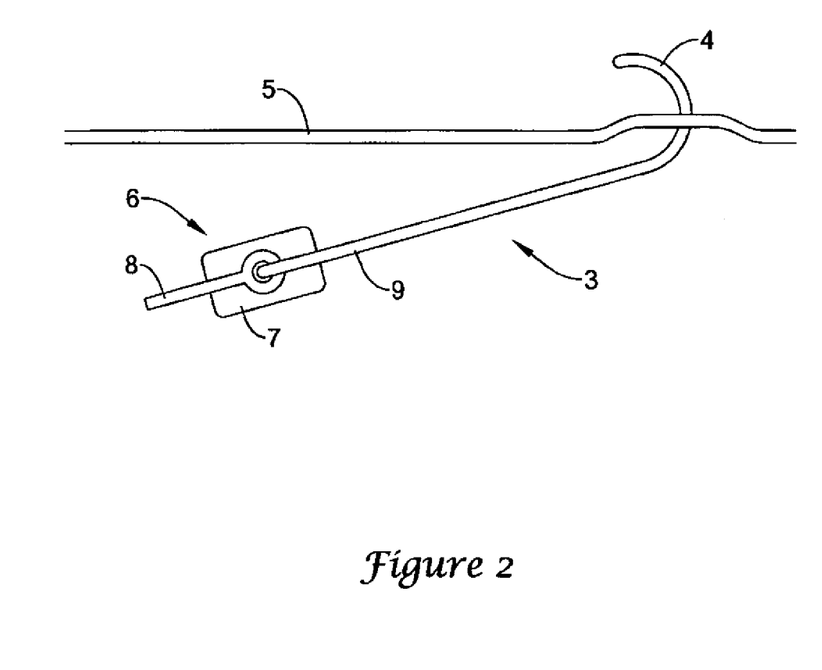
FIG. 2 is a side-view schematic drawing of a strut having a time-degrading connector for reducing its applied radially expanding force and an anchor extending through the vessel wall.
Figure 3:
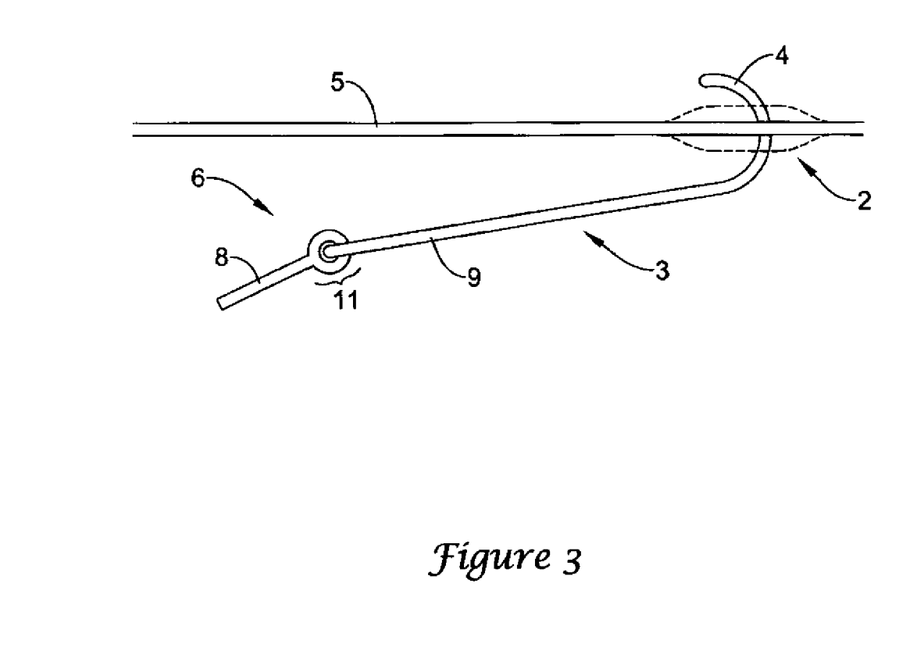
FIG. 3 is a side-view schematic drawing of the strut of FIG. 2, after the biodegradable element has degraded.

FIG. 2 is a side-view schematic drawing of a strut 3 having a time-degrading connector 6 for reducing its applied radially expanding force and an anchor 4 extending through the vessel wall 5. In the design of FIG. 2, the link 11 is encased within the biodegradable element 7. FIG. 3 is a side-view schematic drawing of the strut 3 of FIG. 2, after the biodegradable element 7 has degraded, revealing the link 11.

The time-degrading connector 6 connects the proximal section 8 and distal section 9 of the strut 9. Prior to degrading of the biodegradable element 7, the proximal 8 and distal sections 9 of the strut 3 are held rigidly with respect to each other by the biodegradable element 6. After the biodegradable element 6 has dissolved or softened, the link 11 is free to move, and the proximal 8 and distal sections 9 of the strut 3 are free to pivot with respect to each other. There may be a region of tissue 2 in or around the vein wall 5 that thickened during the degradation of the biodegradable element 6.

In the design of FIGS. 2 and 3, the link 11 includes two interlocking loops, with one loop on the proximal section 8 and the other loop on distal section 9. In the design of FIGS. 2 and 3, the loops are made integral with the proximal and distal sections of the strut 3. In other designs, the loops may be made separately and attached to the proximal and distal sections of the strut 3. The loops may be complete loops, as shown in FIGS. 2 and 3, or one or both may be partial loops or hooks.

In general, the link 11 has a strong resistance to longitudinal movement of the distal section 8 with respect to the proximal section 9, but has a weak resistance to rotational movement of the distal section 8 with respect to the proximal section 9. In this manner, the link 11 can still ensure that the hub 11 remains attached via the struts 3 to the vessel wall 5, even though the radially outward force exerted by the struts is decreased or eliminated.

In some cases, the biodegradable element 7 fully encapsulates the link 11. In other cases, the biodegradable element 7 partially encapsulates the link 11 enough to maintain rigidity along the strut 3 prior to degradation. In other cases, the biodegradable element 7 may be disposed alongside or laterally adjacent to the link 11.

In some cases, it may be desired in advance that the expansile force should be reduced in a prescribed length of time, such as a few days after implantation. These cases may use degradation of the fixation material through exposure to the flow of blood inside the vessel, which can lead to dissolving or softening of the fixation material. This may be known as passive degradation.

In other cases, it may be desirable to actively degrade the fixation material in response to a particular test, in preparation for another medical procedure, or during retrieval of the filter. For instance, a physician may determine that adequate tissue healing has occurred, so that the high expansion anchoring force is no longer needed. For these cases, the fixation material can be softened by an active mechanism, such as wireless heating or a change in pH. Alternatively, the fixation material can be softened during a filter retrieval procedure, such as by applying an electrical or thermal mechanism by a retrieval tool.

Figure 4:
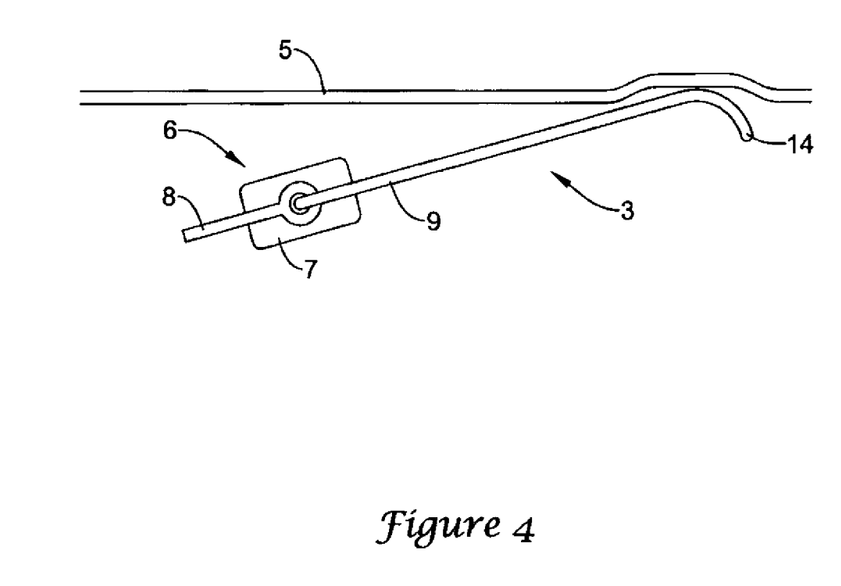
FIG. 4 is a side-view schematic drawing of a strut having a time-degrading connector for reducing its applied radially expanding force and an anchor pushing against the vessel wall.
Figure 5:
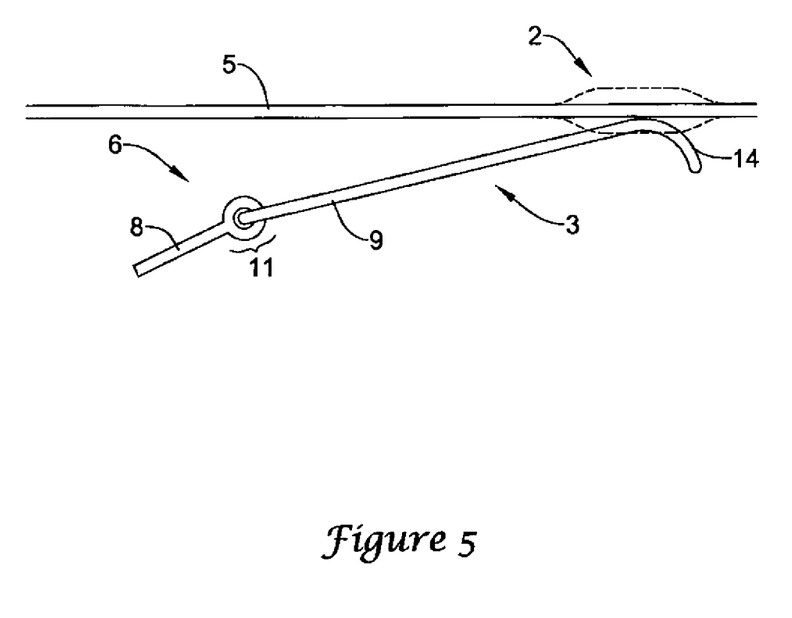
FIG. 5 is a side-view schematic drawing of the strut of FIG. 3, after the biodegradable element has degraded.

The designs in FIGS. 1-3 show the anchors 4 as hooks that penetrate the wall 5 of the vessel. Alternatively, the anchors may contact the interior wall 5 of the vessel without penetrating through it. FIG. 4 is a side-view schematic drawing of a strut 3 having a time-degrading connector 6 for reducing its applied radially expanding force and an anchor 14 pushing against the vessel wall 5. FIG. 5 is a side-view schematic drawing of the strut 3 of FIG. 3, after the biodegradable element 7 has degraded.

For designs in which the penetration of the vein wall is minimal or absent, such as those shown in FIGS. 4 and 5, the device typically uses higher initial expansile forces to stabilize the filter. For example, complete or partial loops that do not penetrate through the vein wall, or a wire or polymer pad with interstices for tissue to grow into or through, and which is initially pressed against the vein wall by expansile forces, are generally incorporated by healing tissue over time. The resulting fibrotic attachment to the vein wall securely anchors the filter without the need for prolonged expansile forces. For these designs, a softening fixation material may produce reduced expansile forces over time.

For the design of FIGS. 4 and 5, note in FIG. 5 the region 2 of thickened tissue at the point of contact between the anchor 14 and the wall 5 of the vessel. At this region 2, the vein is no longer pushed outward by the anchor 14.

Figure 6:
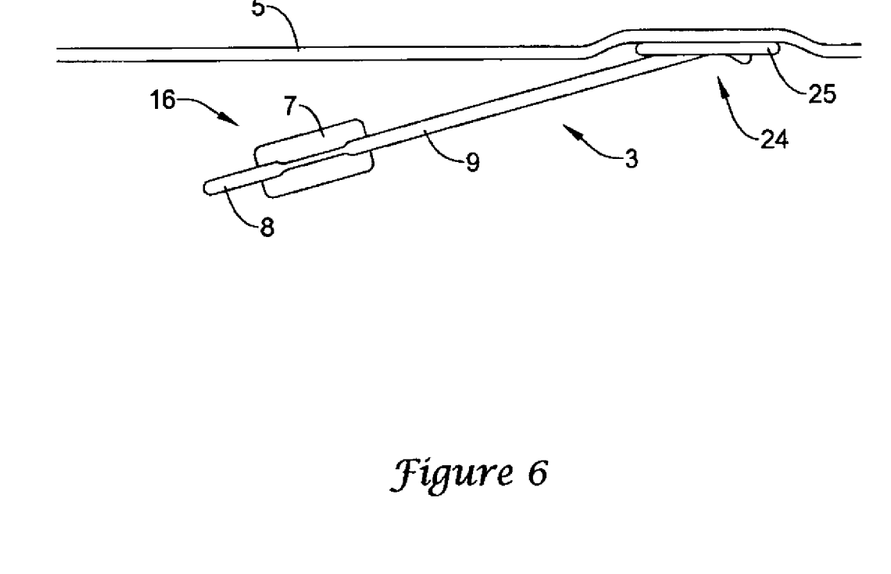
FIG. 6 is a side-view schematic drawing of a strut having a time-degrading connector for reducing its applied radially expanding force and an anchor pushing against a pad on the vessel wall.
Figure 7:
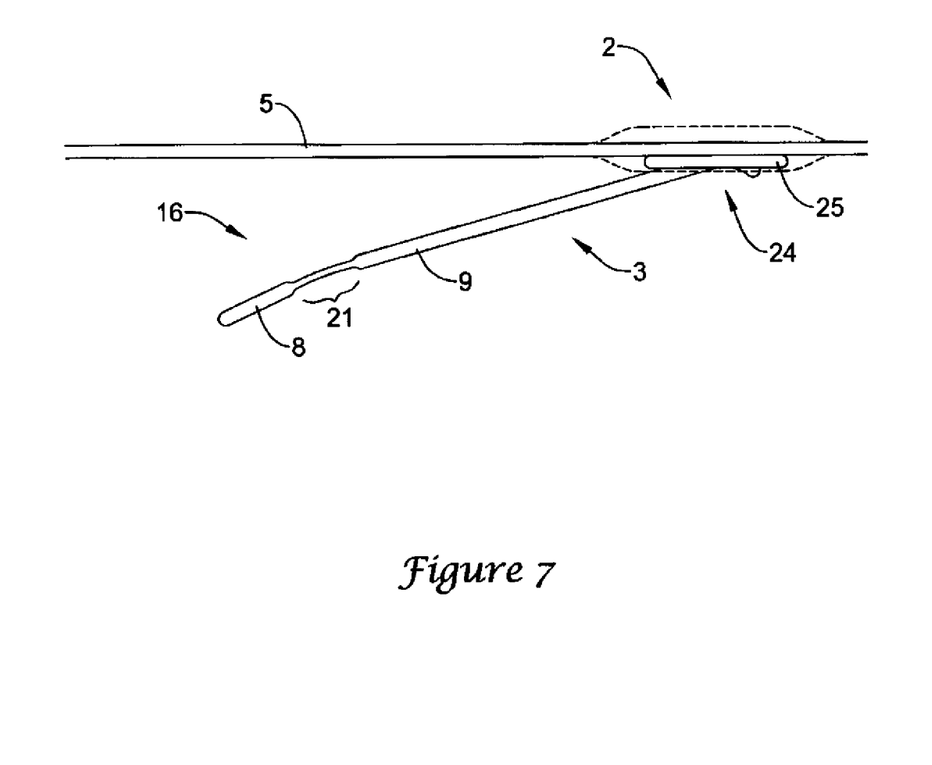
FIG. 7 is a side-view schematic drawing of the strut of FIG. 6, after the biodegradable element has degraded.

The designs in FIGS. 1-5 show the time-degrading connector 6 having a pair of interlocked loops as the link 11. Alternatively, the link 21 may be a narrowed portion of the strut between the proximal section 8 and the distal section 9. FIG. 6 is a side-view schematic drawing of a strut 3 having a time-degrading connector 16 for reducing its applied radially expanding force and an anchor 24 pushing against an anchor pad 25 on the vessel wall 5. FIG. 7 is a side-view schematic drawing of the strut 3 of FIG. 6, after the biodegradable element 7 has degraded.

The link 21 in FIGS. 6 and 7 is a narrowed section of the strut 3, which can bend to permit rotational motion between the proximal 8 and distal 9 sections of the strut 3, but cannot significantly stretch or compress, so that longitudinal motion is inhibited between the proximal 8 and distal 9 sections of the strut 3. In some cases, the narrowed section has a reduced size along a tangential cross-section. In some cases, the narrowed section has a reduced size along a radial cross-section. In some cases, the narrowed section has a reduced size along a tangential cross-section and along a radial cross-section. In some cases, the narrowed section has a circular cross-section along the entire narrowed cross-section. In some cases, the strut 3 has a circular cross-section along the entire strut 3. In some cases, the strut 3 has a rectangular cross-section along the entire strut 3.

Note that for the narrowed section link 21 of FIGS. 6 and 7, the expansile force may be reduced to a finite, non-zero value when the fixation material has completely dissolved or softened, rather than the zero or near-zero value typically attained with the interlocked loop link 11. Such a small but non-zero force may be useful for keeping the filter centered within the vessel.

Note that the design of FIGS. 6 and 7 includes an optional anchor pad 25. It is understood that such an anchor pad 25 may optionally be used with the anchor 14 shown in FIGS. 4 and 5, or with other suitable anchors.

The anchor pad 25 may promote tissue healing and attachment over time, and may be held in place by expansile forces until the fixation material dissolves or softens. While the biodegradable element 7 is dissolving or softening, healing tissue is growing through and around the anchor pad 25 for secure anchoring.

The designs in FIGS. 1-7 show the filter as having a single hub with struts extending in the general distal direction from the hub. In the designs in FIGS. 1-7, each distal end of the respective strut exerts an expansile force against the interior wall of the vessel, either directly or through an anchor pad 25. Alternatively, the filter may have two hubs, with struts that extend from one hub to the other.

Figure 8:
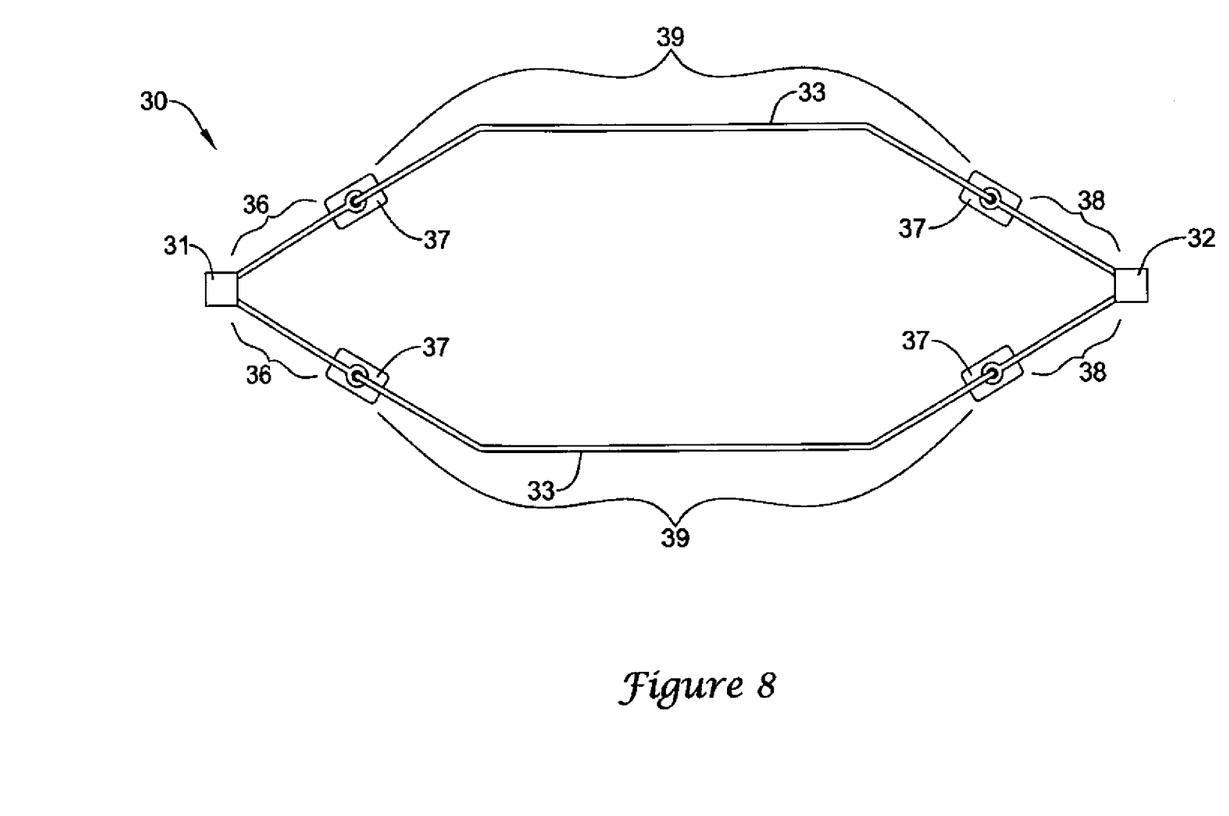
FIG. 8 is a side-view schematic drawing of an intravascular filter having its struts joined at both longitudinal ends, with time-degrading connectors on the struts.

FIG. 8 is a side-view schematic drawing of an intravascular filter 30 having its struts 33 joined at both longitudinal ends, with time-degrading connectors 37 on the struts 33. Two such struts 33 are shown, but it is understood that the filter may have any suitable number of struts 33, such as two, three, four, five, six, seven, eight, nine, ten, or more than ten, that the struts 33 are typically arranged circumferentially within the interior of the vessel, and that the struts 33 are typically uniformly distributed around the circumference of the vessel.

Each strut 31 extends from a proximal hub 31 to a distal hub 32. The struts 33 are arranged to have a proximal section 36 secured to the proximal apical hub 31, a distal section 38 secured to the distal apical hub 32, and a central section 39 between the proximal section 36 and the distal section 38. A central portion 35 of the central section 39 extends generally parallel to a longitudinal axis connecting the proximal 31 and distal 32 apical hubs. The central portions 35 of the struts 33 are arranged circumferentially within an interior of the vessel. The central portions 35 exert an expansile force against the interior of the vessel.

In the design of FIG. 8, each strut 33 includes a biodegradable element 37 between its proximal 31 and central 39 sections; and each strut 33 includes a biodegradable element 37 between its distal 38 and central 39 sections. Alternatively, one of the biodegradable elements 37 may be eliminated, or more may be added along the strut. In some cases, different struts 33 have differently located biodegradable elements 37. In other cases, all the struts 33 have the same configuration for the biodegradable elements 37.

In general, regardless of the number of biodegradable elements 37 along a particular strut 33, each biodegradable elements 37 includes a fixation material that rigidly connects adjacent sections of the strut 33, prior to degradation. The adjacent sections may be proximal and central, central and distal, or other unnamed sections of the strut 33.

The designs in FIGS. 1-8 use a fixation material that is separate from the struts. As an alternative, the filter struts themselves may be softened over time or when desired, such as by changing the temper of a metal strut using local heating, or by changing magnetic forces on elements of the filter apparatus.

The filters shown and described herein may be used for decreasing the outward force of an intravascular device over time, reduced pulmonary embolism, fabricating a vena cava filter and retrieving a vena cava filter. Various elements shown and described herein may be combined in additional configurations and may be combined with other features and enhancements known in the art.

While the embodiments specifically depicted herein illustrate the use of a bioabsorbable centering element in conjunction with intravascular filters, and more specifically blood clot filters, it will be readily apparent that the invention may be applicable to a variety of other intravascular devices implantable within the body. For example, certain aspects of the present invention may be applicable to embolic protection filters, retrieval baskets, laparoscopic devices, endoscopic devices, snares, stents, or other implantable medical devices wherein centering within a vessel may be desired.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

I claim:

1. An intravascular filter for a vessel, comprising:
   a non-biodegradable apical hub;
   a plurality of non-biodegradable struts, each strut having a proximal section secured to the apical hub and a distal section rotatably connected to the proximal section at a link, the distal section extending generally distally away from the apical hub and extending radially outward from a longitudinal axis of the apical hub, the respective distal sections of the struts configured to exert an expansile force against an interior of the vessel; and
   at least one biodegradable element disposed along at least one strut encapsulating the link, the biodegradable element maintaining the expansile force prior to degradation and reducing the expansile force after degradation;
   wherein the distal section is non-unitary with and independent of the proximal section.

2. The filter of claim 1, wherein the biodegradable element comprises a fixation material that rigidly connects the proximal section to the distal section of the respective strut, prior to degradation.

3. The filter of claim 2, wherein prior to degradation, the fixation material fixes in place the link between the proximal section and the distal section, the link having strong resistance to longitudinal movement of the distal section with respect to the proximal section, the link having weak resistance to rotational movement of the distal section with respect to the proximal section.

4. The filter of claim 3, wherein the link comprises a pair of interlocked loops, one loop in the pair fixedly disposed on the proximal section, and the other loop in the pair fixedly disposed on the distal section.

5. The filter of claim 4, wherein the fixation material surrounds the pair of interlocked loops.

6. The filter of claim 2, wherein the fixation material dissolves over time under the influence of blood flow in the vessel.

7. The filter of claim 2, wherein the fixation material softens over time under the influence of blood flow in the vessel.

8. The filter of claim 2, wherein the fixation material softens under the influence of an active softening agent.

9. The filter of claim 8, wherein the active softening agent comprises wireless heating of the fixation material.

10. The filter of claim 8, wherein the active softening agent comprises a change in pH.

11. The filter of claim 8, wherein the fixation material is softened during a procedure for retrieving the filter.

12. The filter of claim 1, wherein each strut exerts the expansile force directly against the interior of the vessel.

13. The filter of claim 1, wherein each strut exerts the expansile force against a respective anchor pad disposed between the strut and the interior of the vessel.

14. The filter of claim 1, wherein each strut includes at least one biodegradable element rigidly connecting the respective proximal section to the respective distal section, prior to degradation.

15. An intravascular filter for a vessel, comprising:
   a non-biodegradable proximal apical hub;
   a non-biodegradable distal apical hub;
   a plurality of non-biodegradable struts,
   each strut having a proximal section secured to the proximal apical hub,
   each strut having a distal section secured to the distal apical hub,
   each strut having a central section between the proximal section and the distal section, the central section coupled to the proximal section by a proximal joint and coupled to the distal section by a distal joint,
   a central portion of the central section extending generally parallel to a longitudinal axis connecting the proximal and distal apical hubs,
   the central portions of the struts configured to be arranged circumferentially within an interior of the vessel,
   the central portions configured to exert an expansile force against the interior of the vessel; and
   wherein each strut includes a biodegradable element disposed at the proximal joint between the proximal and central sections and a biodegradable element disposed at the distal joint between the distal and central sections,
   the biodegradable elements maintaining the expansile force prior to degradation and reducing the expansile force after degradation, the distal section is non-unitary with and independent of the central section, the proximal section is non-unitary with and independent of the central section.

16. The filter of claim 15, wherein each biodegradable element comprises a fixation material that rigidly connects adjacent sections of the strut, prior to degradation.

17. The filter of claim 15, wherein each proximal joint rotatably connects the proximal section to the central section, thereby providing relative rotation therebetween after degradation of the biodegradable element; and
   wherein each distal joint rotatably connects the distal section to the central section, thereby providing relative rotation therebetween after degradation of the biodegradable element.

18. An intravascular filter for a vessel, comprising:
   a non-biodegradable apical hub;
   a plurality of non-biodegradable struts, each strut having a proximal section secured to the apical hub, and a distal section rotatably connected to the proximal section at a link, the distal section extending generally distally away from the apical hub and extending radially outward from a longitudinal axis of the apical hub, the respective distal sections of the struts configured to exert an expansile force against an interior of the vessel; and
   a plurality of biodegradable elements, each biodegradable element in the plurality disposed along a respective strut between the respective proximal section and the respective distal section and encapsulating the link,
   the biodegradable elements comprising a fixation material that, prior to degradation, fixes in place a link between the proximal section and the distal section, the link having strong resistance to longitudinal movement of the distal section with respect to the proximal section, the link having weak resistance to rotational movement of the distal section with respect to the proximal section;

wherein the distal section is non-unitary with and independent of the proximal section.

* * * * *